(12) United States Patent
Wilson Waterworth et al.

(10) Patent No.: US 11,220,690 B2
(45) Date of Patent: Jan. 11, 2022

(54) FORMULATION

(71) Applicant: ATLANTIC PHARMACEUTICALS (HOLDINGS) LTD, Saffron Walden (GB)

(72) Inventors: Toby Wilson Waterworth, Saffron Walden (GB); Lorin Johnson, Los Altos Hills, CA (US); Janette Thomas, Saffron Walden (GB); Michael Webb, Bishop's Stortford (GB)

(73) Assignee: Atlantic Pharmaceuticals (Holdings) LTD, Saffron Walden (GB)

( * ) Notice: Subject to any disclaimer, the term of this patent is extended or adjusted under 35 U.S.C. 154(b) by 0 days.

(21) Appl. No.: 16/476,221

(22) PCT Filed: Jan. 8, 2018

(86) PCT No.: PCT/EP2018/050336
§ 371 (c)(1),
(2) Date: Jul. 5, 2019

(87) PCT Pub. No.: WO2018/127582
PCT Pub. Date: Jul. 12, 2018

(65) Prior Publication Data
US 2019/0367927 A1   Dec. 5, 2019

(30) Foreign Application Priority Data
Jan. 6, 2017   (GB) ..................... 1700257

(51) Int. Cl.
| | | |
|---|---|---|
| C07H 21/04 | (2006.01) |
| C12N 15/113 | (2010.01) |
| A61P 27/02 | (2006.01) |
| A61P 11/06 | (2006.01) |
| A61P 29/00 | (2006.01) |
| A61K 9/00 | (2006.01) |
| A61K 9/06 | (2006.01) |
| A61K 47/02 | (2006.01) |
| A61K 47/14 | (2017.01) |
| A61K 47/38 | (2006.01) |

(52) U.S. Cl.
CPC ........ *C12N 15/1138* (2013.01); *A61K 9/0031* (2013.01); *A61K 9/06* (2013.01); *A61K 47/02* (2013.01); *A61K 47/14* (2013.01); *A61K 47/38* (2013.01); *A61P 11/06* (2018.01); *A61P 27/02* (2018.01); *A61P 29/00* (2018.01); *C12N 2310/11* (2013.01)

(58) Field of Classification Search
CPC .................................................. C12N 15/113
See application file for complete search history.

(56) References Cited

U.S. PATENT DOCUMENTS

| | | |
|---|---|---|
| 5,576,302 A | 11/1996 | Cook et al. |
| 8,168,600 B2 | 5/2012 | Dokka et al. |
| 8,377,897 B2 | 2/2013 | Teng et al. |
| 8,691,785 B2 | 4/2014 | Teng et al. |
| 9,249,413 B2 * | 2/2016 | Schmidts ............... A61P 29/00 |
| 2004/0235164 A1 | 11/2004 | Bennett et al. |
| 2005/0163844 A1 | 7/2005 | Ashton |
| 2005/0238606 A1 | 10/2005 | Dokka et al. |
| 2007/0135364 A1 | 6/2007 | Bennett et al. |
| 2007/0249551 A1 | 10/2007 | Teng et al. |
| 2008/0152654 A1 * | 6/2008 | Reich ..................... A61P 27/00 424/145.1 |
| 2009/0275631 A1 | 11/2009 | Wedel |
| 2013/0274309 A1 | 10/2013 | Teng et al. |
| 2017/0051290 A1 | 2/2017 | Byrne et al. |

FOREIGN PATENT DOCUMENTS

| | | |
|---|---|---|
| WO | 95/04749 A1 | 2/1995 |
| WO | 99/61462 A1 | 12/1999 |
| WO | 00/18907 A1 | 4/2000 |
| WO | 2004/108945 A2 | 12/2004 |
| WO | 2005/023761 A2 | 3/2005 |
| WO | 2006/060649 A2 | 6/2006 |
| WO | 2010/111497 A2 | 9/2010 |
| WO | 2013/123996 A1 | 8/2013 |
| WO | 2015/166263 A1 | 11/2015 |

OTHER PUBLICATIONS

Wikipedia (Wikipedia contributors. "Saline (medicine)." Wikipedia, The Free Encyclopedia. Wikipedia, The Free Encyclopedia, Nov. 2, 2020. Web. Nov. 5, 2020).*
Rahul C. Mehta et al., *Intercellular Adhesion Molecule-1 Suppression in Skin by Topical Delivery of Anti-Sense Oligonucleotides*, The Society for Investigative Dermatology, Inc., 2000, pp. 805-812.
Bruce R. Yacyshyn et al., *A Placebo-Controlled Trial of ICAM-1 Antisense Oligonucleotide in the Treatment of Crohn's Disease*, Gastroenterology 1998, vol. 114, pp. 1133-1142.
P. B. Miner Jr. et al., *Bioavailability and Therapeutic Activity of Alicaforsen (ISIS 2302) Administered as a Rectal Retention Enema to Subjects with Active Ulcerative Colitis*, Aliment Pharmacol Ther. vol. 23, 2006, pp. 1427-1434.
Andrew T. Gerwirtz et al., *Current Opinion in Investigational Drugs*, Alicaforsen ISIS Pharmaceuticals, 2001, vol. 2, No. 10, pp. 1401-1406.
P. B. Miner, *Response of the Gastrointestinal & Pulmonary Symptoms of Churg-Strauss Syndrome*, AJG, vol. 99, No. 10, 2004, pp. 2, Abstract.
William R. Shanahan Jr., *ISIS 2302, An Antisense Inhibitor of Intercellular Adhesion Molecule 1*, Expert Opinion Invest. Drugs, 1999, vol. 8, No. 9, pp. 1417-1429.
P. B. Williams et al., *Primate Model for Penetrating Karatoplasty*, Investigative Ophthalmology & Visual Science, May 2003, vol. 44, 1392.
SEQ ID N0:1 Search; identical match with U.S. Pat. No. 5,576,302 (Year: 2020).

* cited by examiner

*Primary Examiner* — Kimberly Chong
(74) *Attorney, Agent, or Firm* — Workman Nydegger

(57) ABSTRACT

The present invention relates to a new formulation of the oligonucleotide of SEQ ID NO:1.

23 Claims, 12 Drawing Sheets

Specification includes a Sequence Listing.

A. Delta G: −3.9 kcal/mole  Base Pairs 3
   5'            TCGTCGTTTTGTCGTTTTGTCGTT   ODN-2006
                  . :   |||
   3' ACTGCCTACGGTCGAACCCG                  Alicaforsen B. Delta G: −6.3 kcal/mole  Base Pairs: 4
   5'         GCCCAAGCTGGCATCCGTCA    3'  Alicaforsen
                  :  || ||  :
   3' ACTGCCTACGGTCGAACCCG            5'  Alicaforsen

Fig 4

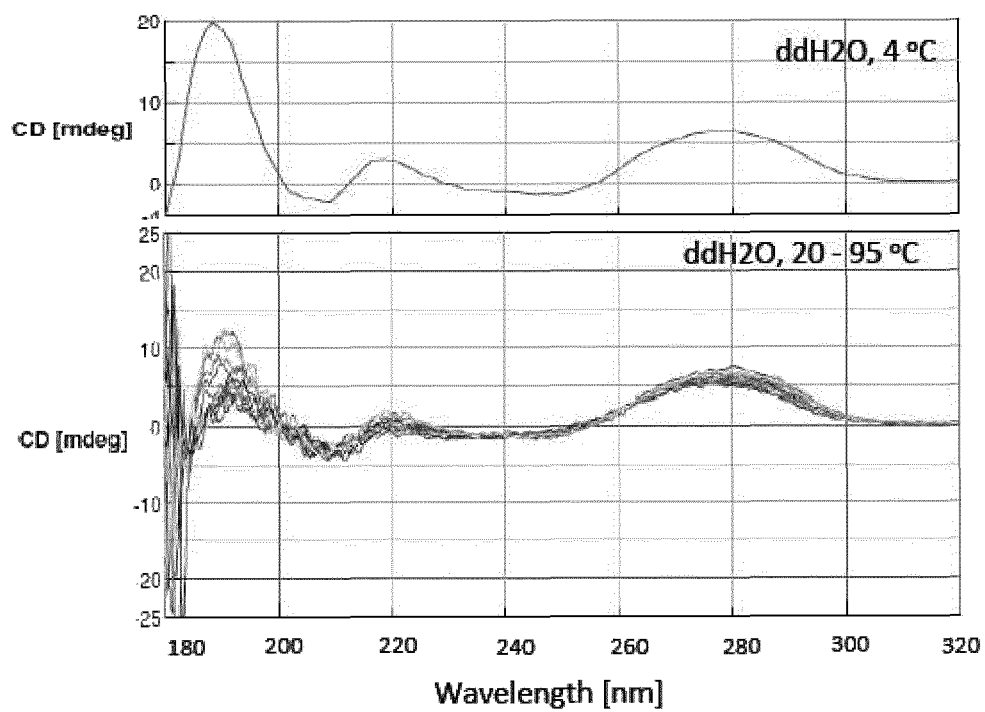
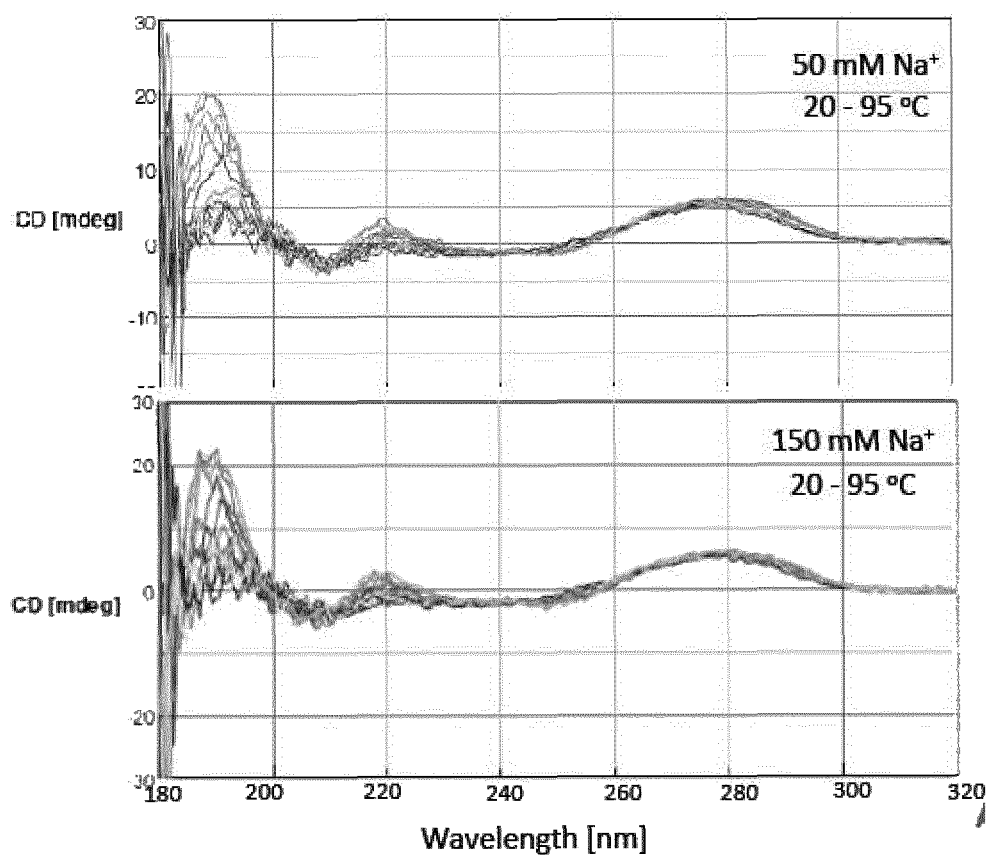
Fig 6

Fig 7 (a) and (b)

FORMULATION

BACKGROUND OF THE INVENTION

1. The Field of the Invention

The present invention relates to a new formulation of the oligonucleotide of SEQ ID NO:1.

2. The Relevant Technology

Mucosal surfaces represent the first interface between the internal environment of the host organism and the external environment. Mucosal surfaces are therefore enriched in a variety of cellular and acellular structures that protect the host from foreign pathogen or antigen exposure. These important surfaces are represented by the mucosal surfaces of the oral and nasal (sinus) cavity, the pulmonary and digestive systems and mucosal tissues surrounding the eye.

The cells comprising the mucosa are equipped to sense and respond to a variety of foreign substances. These cells also elaborate a variety of molecular pathways to communicate such invasion to the surrounding tissues and recruit an influx of additional inflammatory and immune cells to fight the infection, repair damage and if necessary induce specific immune responses in the form of antibodies. While these mechanisms serve an important and indeed life-saving function for the organism, their chronic and/or misguided activation can lead to considerable morbidity and mortality.

The chronic influx of inflammatory cells and the subsequent local activation of cells of the immune system are two primary loci where chronic mucosal inflammation can be controlled. These responses are part of the "innate immune system". The first responding cells of the innate immune system, such as dendritic cells and macrophages, ingest pathogens and release cytokines drawing secondary, active and defensive cells from the blood. These secondary invading cells must be "drawn to" the site of inflammation by molecules on the surface of cells lining the local blood vessels (vascular endothelium). Such molecules are themselves expressed in response to cytokines released at the initial pathogen invasion site. These molecules bind to receptors on circulating blood cells and allow local adhesion and subsequent diapedesis into the invasion site. The adhesion molecules are known as intracellular adhesion molecules (ICAM) and a variety of these have been discovered. Blocking the expression and/or function of the various ICAM's has led to the development of several therapeutic products to suppress inflammatory diseases.

Cells of the innate immune system also have a well-developed repertoire of surface receptors that sense and bind microbial components expressed by bacteria, viruses, fungi and other pathogens. These receptors have been termed "toll-like receptors" (TLR's) and as many as 12 members of this family are now known in the human genome. Pathogen-encoded TLR ligands fall into three broad categories: lipids and lipopeptides (TLR2/1; TLR2/6 and TLR4), proteins (TLR5 and TLR11) and nucleic acids (TLR3, 7, 8 and 9). Therapeutic targeting of certain TLR's has been exploited as a means to stimulate the immune system (vaccine production) and agents targeting other TLR's are being developed to inhibit certain immune functions.

An ideal therapeutic agent to target and control mucosal inflammation would therefore be an agent with both acute and long-lasting effects on mucosa inflammation and may indeed be disease altering.

SUMMARY OF THE INVENTION

The present invention addresses this.

The present invention relates to, as a first aspect, a pharmaceutical composition comprising SEQ ID NO:1 with a cation optionally selected from the following list $Na^+$, $K^+$, $Mg^+$, $Ca^{++}$, $Ba^{++}$, $Mn^{++}$, $Ni^{++}$, $Zn^{++}$ and $Cr^{+++}$, preferably $Na^+$, more preferably 40-200 mM $Na^+$ optionally including 2-20 mM $Mg^{2+}$. The concentration range is preferably 40-200 mM for $Na^-$ or $K^-$, and 2-20 mM for $Mg^{++}$, $Ca^{++}$, $Ba^{++}$, $Mn^{++}$, $Ni^{++}$, $Zn^{++}$ or $Cr^{+++}$. For example, the pharmaceutical composition may have a combination of 40-200 mM $Na^+$ and 2-20 mM $Mg^{2+}$, or 40-200 mM $Na^+$ and 40-200 mM $K^+$. For example the composition may comprise a combination of $Na^+$ and $K^+$, or $Na^+$ and $Mg^{++}$ or $Na^+$ and $Ca^{++}$ or $Na^+$ and $Ba^{++}$ or $Na^+$ and $Mn^{++}$ or $Na^+$ and $Ni^{++}$ or $Na^+$ and $Li^{++}$ or $Na^+$ and $Zn^{++}$ or $Na^+$ and $Cr^{++}$, or $K^+$ and $Mg^{++}$ or $K^+$ and $Ca^{++}$ or $K^+$ and $Ba^{++}$ or $K^+$ and $Mn^{++}$ or $K^+$ and $Ni^{++}$ or $K^+$ and $Li^{++}$ or $K^+$ and $Zn^{++}$ or $K^+$ and $Cr^{+++}$.

The composition of the first aspect may also comprise one or more of hydroxymethyl cellulose, methyl paraben sodium, propylparaben sodium, monobasic sodium phosphate monohydrate, sodium hydroxide, hydrochloric acid and/or water.

The composition may be in the form of a liquid syrup, gel, film, cream, powder, tablet, enema and/or particulate, preferably which is suitable for inhalation.

The composition of the invention may be formulated as a gel, cream, lotion, solution, suspension, emulsion, ointment, powder or particulate which is suitable for inhalation, tablet, spray, aerosol, foam, salve, microparticle, nanoparticle, or bioadhesive, and may be prepared so as to contain liposomes, micelles and/or microspheres.

The composition may have the components in the following ranges

| | |
|---|---|
| SEQ ID NO: 1 | 4 mg |
| hydroxymethyl cellulose | 7-8 mg, optionally 7.5 mg |
| methylparaben sodium 16.6 mM | 2.8-3.0 mg |
| propylparaben sodium 1.4 mM | 0.28-3 mg |
| monobasic sodium phosphate monohydrate37.5 mM | 4.4-4.6 mg | wherein the ranges given are per ml with a total of 60 ml per dose. Thus, in a treatment of 240 mg in 60 ml, the treatment is 4 mg/ml. The above specific dose may be a liquid enema formulation.

A second aspect of the invention relates to the composition of the first aspect for use in medicine. The medicine may be human or veterinary. Veterinary medicine includes any animal including production and/or pet animals including, in particular dogs, cats and/or equine animals.

According to the second aspect of the invention, the medicine may be for the prevention or treatment of inflammatory bowel disease, rectal stump disease, radiation-induced proctitis, pouchitis, asthma, inflammation of the eye, dry eye, rhinitis or sinusitis or graft versus host disease.

A third aspect of the invention is the use of SEQ ID NO:1 in the manufacture of a medicament according to the first aspect of the invention for the prevention or treatment of inflammatory bowel disease, rectal stump disease, radiation-induced proctitis, pouchitis, asthma, inflammation of the eye, dry eye, graft versus host disease (GVHD), rhinitis or sinusitis.

All features of the first aspect of the invention also apply to the third aspect.

A fourth aspect of the invention relates to a method of treating inflammatory bowel disease, rectal stump disease, radiation-induced proctitis, pouchitis, asthma, inflammation of the eye, dry eye, rhinitis, sinusitis, or grant-versus host disease, the method comprising administration of a composition of the first aspect of the invention to a patient in need thereof.

All features of the first aspect of the invention also apply to the fourth aspect. The patient may be a human (adult or youth) or an animal.

A fifth aspect of the invention relates to a method of making a composition of the first aspect of the invention, the method comprising combining SEQ ID NO:1 with a cation, optionally selected from the following list Na$^+$, Na$^+$, Mg$^{++}$, Ca$^{++}$, Ba$^{++}$, Mn$^{++}$, Ni$^{++}$, Li$^{++}$, Zn$^{++}$, and Cr$^{+++}$, preferably Na$^+$, more preferably 40-200 mM Na$^+$, optionally including 2-20 mM Mg$^{2+}$.

Methods for making this new composition are standard methods as known in the art.

The invention provides a composition, according to the first aspect of the invention, as claimed in any one of claims 1 to 6, wherein the composition is in the form of an enema and wherein the composition is formulated in a dosage form to provide a concentration of SEQ ID NO:1 at 4 mg/ml per day.

The composition may be in the form of an enema and wherein the composition is formulated in a dosage form to provide a concentration of SEQ ID NO:1 at 0.25-4 mg/ml per day.

```
SEQ ID NO: 1 is as follows:
5'-gcccaagctg gcatccgtca-3'.
```

The antisense oligonucleotide SEQ ID NO:1 is also known as alicaforsen.

Certain enhancements to the formulation containing the oligonucleotides of SEQ ID NO:1 may also be necessary to aid in the retention of the active ingredient at the site of application. For example, the formulation can be prepared using components that cause the formulation to be a liquid at room temperature, but solidify to a gel state at body temperature. In other instances, the formulation may be prepared as a liquid and applied to a mucosal surface, such as the nasal mucosa, followed by the application of an inert dry powder, such as methyl cellulose, to retain the formulation at the site of application. In other instances, a dry powder formulation of the composition may be mixed with the inert dry powder and applied together at the mucosa site.

The oligonucleotides SEQ ID NO:1 in accordance with this invention preferably comprises from about 20 to about 80 nucleic acid base units. It is more preferred that such oligonucleotides comprise from about 20 to 50 nucleic acid base units, still more preferred to have from about 20 to 30 nucleic acid base units, and most preferred to have from about 20 to 22 nucleic acid base units. As will be appreciated, a nucleic acid base unit is a base-sugar combination suitably bound to an adjacent nucleic acid base unit through phosphodiester or other bonds. One skilled in the art will understand that about 20 to about 80 nucleic acid base units includes 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleobase units.

In a further embodiment, the composition comprises a fragment of SEQ ID NO:1, wherein the fragment is at least 8, 9, 10, 11, 12, 13, 14, 15, 16, 17, 18 or 19 nucleotides in length. The fragment can hybridise to a sequence in the 3'-untranslated region of the human ICAM-1 mRNA. The fragment can hybridise under moderate or stringent conditions with nucleotides 'cctgacg gatgccagct tgg' (SEQ ID NO:2). Fragments include 'cccaagctg gcatccgtca' (SEQ ID NO:3), 'gcccaagctg gcatccgtc' (SEQ ID NO:4) and 'gcccaagctg gca' (SEQ ID NO:5).

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

As herein defined, "Stringent conditions" or "highly stringent conditions", may be identified by those that: (1) employ low ionic strength and high temperature for washing, for example 0.015 M sodium chloride/0.0015 M sodium citrate/0.1% sodium dodecyl sulphate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 [mu]g/ml), 0.1% SDS, and 10% dextran sulphate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulphate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

As used herein, conditions of moderate or high stringency can be readily determined by those having ordinary skill in the art based on, for example, the length of the DNA. The basic conditions are set forth by Sambrook et al. Molecular Cloning: A Laboratory Manual, 2 ed. Vol. 1, pp. 1.101-104, Cold Spring Harbor Laboratory Press, (1989).

The oligonucleotide can be modified to comprise at least one phosphorothioate linkage. Phosphorothioate modification of the oligonucleotide, by substituting a sulfur molecule for a non-bridging oxygen molecule in each phosphodiester linkage, significantly increases exonuclease resistance relative to unmodified DNA and prolongs the drug half-life (Geary et al., Anti-Cancer Drug Design, 12:383-94, 1997). Phosphorothioate oligonucleotides are only minimally antigenic, non-cytotoxic and well tolerated, and their pharmacokinetic and pharmacodynamic properties are well characterized (see e.g., Butler et al., Lab. Invest, 77:379-88, 1997; Mirabelli et al., Anti-Cancer Drug Des., 6:647-61, 1991). In addition to phosphorothioate backbone modifications, a number of other possible backbone, sugar and other modifications are well known to those skilled in the art.

The actual amount administered, and rate and time-course of administration, will depend on the nature and severity of what is being treated. Prescription of treatment, e.g., decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

For example, in one embodiment, a suitable dose may be 2 mg/ml per day for example, per enema.

In another embodiment, a minimum dose would be 0.25 mg/mL per day for example, per enema.

The composition may be administered once, twice, three or four times a day or periodically.

The composition can be administered for 2, 3, 4, 5, 6, 7, 8 or more weeks.

For example, in one embodiment, a suitable dose per treatment may be 0.05 mg to 400 mg. A treatment can be administered from once to eight times per day.

A suitable dose concentration may be 0.5 mg/mL to 10 mg/mL. A suitable dose administered to asthma patients may be between 0.5 to 5 ml, in particular around 1 mL. A suitable dose administered to dry eye or inflammation of the eye patients may be between 1-100 ul, in particular around 50 ul. A suitable enema administered dose may be between 10 to 100 mL, in particular around 60 mL.

The composition may be administered once, twice, three, four, five, six, seven or eight times a day or periodically.

The composition can be administered for 1, 2, 3, 4, 5, 6, 7, 8 or more weeks.

The composition can be administered for 1, 2, 3, 4, 5 or 6 days.

The composition may be in respect of existing aggravation, inflammation, pain and/or discharge of the effected site or may be prophylactic (preventative treatment). Treatment may include curative, alleviation or prophylactic effects.

Specific examples of diseases treatable by the invention include the mucosal inflammatory conditions described below. Each disease requires the influx of certain blood borne inflammatory cells and activation of immune cells that have localized to the site of inflammation. Such diseases are therefore ideally treated by an agent that can block both the influx of inflammatory cells and the activation of the innate immune system, as provided by the present invention.

Inflammatory bowel diseases include ulcerative colitis (UC) and Crohn's disease (CD), both of which are inflammatory disorders of the intestinal mucosa. Ulcerative colitis is confined to the large intestine, while Crohn's disease can involve any region of the intestinal mucosa, including the oral cavity. Both UC and CD are characterized by the influx of inflammatory and immune cells in response to environmental and autoimmune stimuli. Although the histopathology of the two diseases differ, many therapeutic agents are used to treat both conditions, such as steroids, anti-TNF antibodies and mesalamine.

Pouchitis is inflammation of the distal intestinal mucosa remaining after surgical removal of the colon and formation of a J-pouch by ileal-anal anastomosis. Mucosal inflammation in pouchitis is similar to that observed in ulcerative colitis, although it may have microbial involvement to a greater extant. It is characterized by influx of activated inflammatory cells and activation of the local immune system.

Rectal stump disease is an inflammatory condition affecting the rectal mucosa remaining after colectomy.

Asthma is a complex and multifactorial disorder typified by episodes of breathlessness and wheezing in concert with airway hyper-reactivity (AHR) to a range of stimuli. Chronic inflammation mucosa of the airway wall is thought to be the primary factor driving asthmatic exacerbations. It is now well established that polarized CD4 T helper 2 (Th2) cells infiltrate and accumulate in the bronchial mucosa of allergic asthmatics, and that cytokines secreted from these cells (interleukin-(IL)-4, IL-5, IL-9 and IL-13) are largely responsible for acute exacerbations and promotion of the pathologic features of allergic asthma. Inhibiting the influx of inflammatory cells, through down-regulation of ICAM-1 and suppression of the innate immune response through inhibition of TLR-9 is an effective therapeutic approach provided by the present invention. This was a surprising discovery as several studies have identified TLR9 agonists as a potential therapy for asthma. Several clinical trials have explored the use of TLR9 agonists to treat asthma, for example, Astra Zeneca have a TLR9 agonist AZD1419, in-licensed from Dynavax, in Phase 2a for patients with eosinophilic, moderate to severe asthma via inhaled route. The TLR9 agonist suppresses Th2 (late phase) responses and enhanced Th1 responses. Cytos Biotechnology has run clinical trials using the TLR-9 agonist CYT003-QbG10 to treat allergic bronchial asthma. Other TLR9 agonists which have been evaluated in the clinic for treating asthma were AIC (Dynavax), AVE0675 and SAR-21609 (Sanofi-Aventis/Coley Pharmaceuticals); QAX-935 (Idera Pharmaceuticals/Novartis).

Eosinophilic sinusitis (ES) is an inflammation of the nasal mucosa characterized by the chronic influx of eosinophils and other monocytes and lymphocytes from the blood into the nasal mucosa in response to environmental antigens. This reaction leads to a variety of symptoms including nasal discharge (rhinorrea), congestion, nasal polyps. Eosinophilic sinusitis includes sinusitis and rhinitis. A paper by Licari A et al., (International Journal of Immunopathology Pharmacology, 2014 October-December; 27(4):499-508) explains how the upper and lower airways may be considered as a unique entity, interconnected by coexisting inflammatory processes that share common etiopathogenic mechanisms. The paper explains how previous studies have strongly demonstrated a relationship between rhinosinusitis and asthma. This has led to the introduction of the concept of 'United Airways', which has also been included in the WHO document Allergic Rhinitis and its Impact on Asthma (ARIA); this concept has important consequences also on the treatment of these disorders. The present invention is used to treat eosinophilic sinusitis.

Graft versus host disease occurs subsequent to bone marrow transplantation performed for treatment of blood cell cancers such as leukemia. During transplantation, the host blood-cell forming organs are eliminated by radiation treatment and the donor (graft) marrow transplanted to re-establish the organ's function. While this procedure can effectively treat the cancer, the transplanted immune system can begin to "reject" the host tissues. Sensitive tissues include the liver, skin, lungs and the GI tract. Systemic immunosuppression is used to control the rejection in most of these tissues, but the GI mucosa is particularly difficult to treat with systemic therapies. Inflammation occurring in the small intestine and colon is better treated with targeted therapy delivered directly to the gut lumen. The present invention in either an oral formulation or rectal enema formulation is used to suppress graft versus host disease.

In a paper by Calcaterra et al, in the Journal of Immunology, (2008, 181, 6132-6139) the authors demonstrate that inhibition of TLR9 may lead to the treatment of GVHD. The authors used C57BL/6 knockout mice to demonstrate that when TLR9 knockout mice were used as graft recipients, survival improved compared to wild type recipient mice. Mice were myeloablative-irradiated and injected with $10^7$ bone marrow cells and $4\times10^7$ splenocytes obtained from full MHC major and minor Ag-disparate BALB/c donors. Recipient mice were monitored for clinical signs of GVHD, weight and survival. Interestingly those mice with a TLR4 knockout did not show an improved survival versus wild type recipient mice. All wild-type and TLR4−/− mice succumbed to severe acute GVHD within 60 days, while TLR9−/− mice showed a significantly higher survival rate, with four of eight mice still alive at the end of the experiment. The GVHD clinical score in TLR9−/− mice was also significantly lower than that in TLR 4−/− and C57B/6 mice and this correlated with reduced intestinal damage in the small intestine and to a lesser effect in the large bowel in TLR9−/− mice. Finally, at the end of the experiment, all TLR9−/− surviving mice achieved complete immune reconstitution, showed 100% donor peripheral blood lymphocyte cells. The results in this paper demonstrate the important role that TLR9 plays in the pathogenesis of GVHD.

Inflammation of the eye can also be treated with the present invention. Such conditions are dry eye or Sjogren's disease where reduction in the production of tear fluid results in local inflammation of the ocular mucosa. Dry eye disease is a common complaint of ophthalmic patients. Unaddressed conditions of dry eye can lead to erosion and abrasion of the epithelial cell surface of the cornea, raising susceptibility to infection. Progression of the disease can lead to ulceration of the cornea, even loss of sight. Disease and some physical conditions can predispose individuals to dry eye disorder, including; allergies, diabetes, lacrimal gland deficiency, lupus, Parkinson's disease, Sjogren's syndrome, rheumatoid arthritis, rosacea, and others. Medications for other diseases may cause or exacerbate dry eye disorders, including diuretics, antidepressants, allergy medications, birth control pills, decongestants and others. Age related changes may induce or exacerbate dry eye as well. Post-menopausal women experience changes in hormonal levels that can instigate or worsen dry eye and thyroid imbalances may cause similar changes. Finally aging itself can cause reduction in lipid production with resultant dry eye.

The present invention can be used for treating dry eyes, chronic dry eye (CDE) disease, or dry eye syndrome in a subject in need thereof. Subjects suffering from dry eyes, chronic dry eye (CDE) disease, or dry eye syndrome can be identified by any or a combination of diagnostic or prognostic assays known in the art. For example, typical symptoms of dry eyes, chronic dry eye (CDE) disease, or dry eye syndrome include, but are not limited to, symptoms such as, e.g., stinging, burning, or scratchy sensation in the eyes, stringy mucus in or around the eyes, increased eye irritation from smoke or wind, eye fatigue, sensitivity to light, eye redness, sensation of foreign object in the eyes, difficulty wearing contact lenses, periods of excessive tearing, swollen eyes, eye discomfort, eye pain, and blurred vision (which worsens at the end of the day or after focusing for a prolonged period).

In some embodiments, dry eyes is diagnosed by the tear osmolarity test. The tear osmolarity test measures the number of solid particles in a tear. The higher the tear osmolarity typically indicates that the tear has less water and more particles, e.g., salts, proteins, lipids, and mucin. A tear osmolarity score of below 308 mOsms/L is normal, 308-320 mOsms/L is mild dry eyes, 320-340 mOsms/L is moderate dry eyes, and above 340 mOsms/L is severe dry eye. The present invention can be used to treat mild dry eyes, moderate dry eyes, moderate to severe dry eyes and severe dry eyes.

Symptoms of severe dry eye may include, amongst others, conjunctival injection (hyperemia); such as bulbar conjunctival hyperemia, inferior tarsal conjunctival hyperemia, nasal bulbar conjunctival hyperemia; lid margin hyperemia, central corneal staining and redness of the eye.

More specifically, treatment includes "therapeutic" and "prophylactic" and these types of treatment are to be considered in their broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Prophylactic" also includes preventing reoccurrence of a particular condition in a patient previously diagnosed with the condition. "Therapeutic" may also reduce the severity of an existing condition.

In summary, the present invention provides details describing that:
  Mucosal inflammation can be more effectively treated by agents that can target multiple pathways in the innate immune system.
  Blocking the influx of inflammatory/immune cells (ICAM-1) and blocking the activation of the innate immune response (TLR-9) together allows both an acute and durable response.
  The 20-base oligonucleotide SEQ ID NO:1 known to block ICAM-1, exerts both an acute and durable response because it also inhibits the activation of TLR-9.
  The primary sequence of SEQ ID NO:1 does not predict its action as a TLR-9 antagonist.
  The specific primary sequence of SEQ ID NO:1 suggests possible secondary structures that could influence TLR-9 activity, but does not predict the most stable or optimal structures.
  Conditions that influence the secondary structure of SEQ ID NO:1 also influence its activity as a TLR-9 antagonist.
  It has been discovered that an oligonucleotide, with the primary sequence of SEQ ID NO:1, when submitted to conditions that optimize its secondary structure, is a more potent treatment agent for mucosal inflammation than predicted by the primary sequence alone.

TLRs are a key means by which the host recognizes and mounts an immune response to foreign molecules. They also provide a mechanism by which the innate and adaptive immune responses are linked. Specifically, TLR-9 recognizes bacterial and viral DNA through certain unmethylated CpG motifs not present in mammalian DNA. Cells contained within the mucosa can therefore "sense" and respond to the presence of "foreign" DNA. Binding of such ligands activates the immune system to further respond to and remove the pathogen.

It is also known that synthetic oligonucleotides (ODN) containing CpG dinucleotide sequences can stimulate immune responses through the TLR-9 pathway. In addition, the use of synthetic oligonucleotides has shown utility as inhibitors of inflammatory cytokines and these actions are known to be mediated though inhibitory actions on TLR-9.

The published literature documenting the properties of DNA oligonucleotides required for binding to TLR-9 is extensive and has focused on both agonist and antagonist sequences. While the CpG motif is known to be required for stimulatory activity, there are no canonical sequences known to absolutely predict antagonist sequences. Certain inhibitors have been described previously in the art. In addition to these triplet-containing inhibitory ODNs, several groups have reported other specific DNA sequences that could inhibit TLR-9 mediated activation by CpG containing ODNs. These "inhibitory" or "suppressive" motifs are rich in poly "G" (e.g., "GGG") or "GC" sequences, tend to be methylated and are present in the DNA of mammals and certain viruses. Other inhibitory sequences have been identified as containing a "GGGG" motif within the sequences. Certain repetitive TTAGGG elements, present at high frequency in mammalian telomeres, have been observed to down-regulate CpG-induced immune activation demonstrate that synthetic oligonucleotides containing the TTAGGG element mimic this activity and could be effective in the prevention/treatment of certain Th1-dependent autoimmune diseases.

The secondary structure of ODNs has also been studied as a basis for defining the DNA structure necessary for binding to TLR-9. However, there does not appear to be a secondary structure that absolutely specifies binding affinity, although sequence specific effects on structure are observed to alter the ODN agonist or antagonist activity.

The surprising finding is that SEQ ID NO:1 is an antagonist of TLR-9 and is devoid of agonist activity. Further, the invention defines specific conditions that contribute to the predicted secondary structure of SEQ ID NO:1 and relate the secondary structure to TLR-9 antagonism.

BRIEF DESCRIPTION OF THE DRAWINGS

The following figures are part of the application, where;
FIG. 4 is a thermodynamic predication of duplex stability for SEQ ID NO:1 and ODN2006 hetero duplex vs SEQ ID NO:1 homo duplex.
FIG. 6 shows: Upper-CD spectra of SEQ ID NO:1 in ddH20 at 4° C. Lower-spectra 20-95° C.

DETAILED DESCRIPTION OF THE PREFERRED EMBODIMENTS

The present invention provides the following examples which are not limiting.

EXAMPLES

Example 1: TLR-9 Inhibitory Activity

SEQ ID NO:1 was screened for dose response activity to determine possible EC50 for TLR9 activation at seven different doses (0.01, 0.05, 0.1, 0.5, 1, 5 and 10 µM) in triplicate. Briefly, the TLR9/NF-kB luciferase reporter HEK 293 cell line (Abeomics, San Diego, Calif.) was plated in 96-well white solid plates at $5\times10^4$ cells per well for 16 h. Cells were treated with different doses of SEQ ID NO:1 as well as with 20 ug/ml of CpG ODN-2006, a known agonist of TLR-9 in triplicate for 16 h. Luciferase activity was then measured and analyzed.

Figure 1:
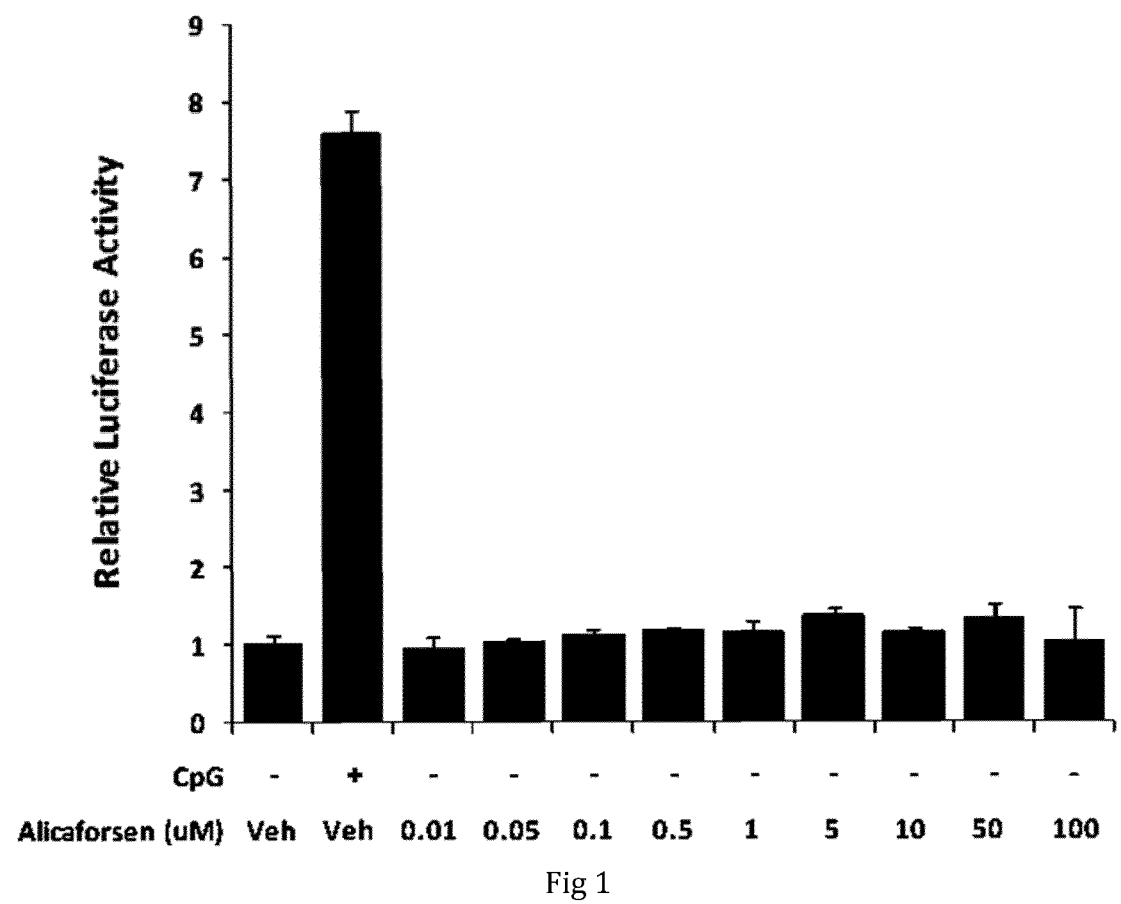
FIG. 1 is a dose response graph for SEQ ID NO:1 stimulation of TLR-9.

As shown in FIG. 1, SEQ ID NO:1 was devoid of agonist activity up to concentrations as high as 100 uM while a 1.0 uM dose of ODN2006 produced a 7.5-fold increase in TLR-9 induced gene activation.

Figure 2:
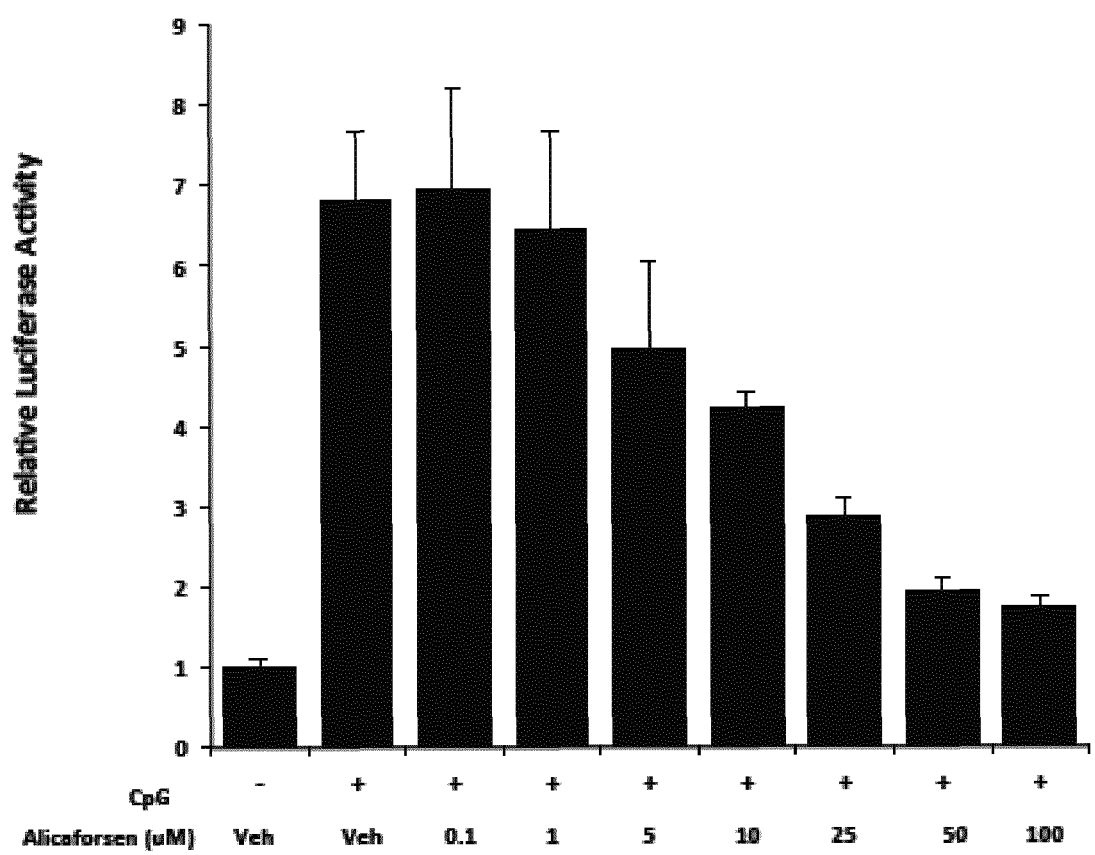
FIG. 2 is a dose response of TLR-9 inhibition by SEQ ID NO:1.

SEQ ID NO:1 was next screened for dose responsive inhibition activity to determine the IC50 against TLR9-mediated NF-kB induction at seven different doses (0.1, 1, 5, 10, 25, 50 and 100 µM) in triplicate. Briefly, the TLR9/NF-kB luciferase reporter HEK 293 cell line was plated in 96-well white solid plates at $5\times10^4$ cells per well for 16 h. Cells were pretreated with different doses of SEQ ID NO:1 in triplicate for 1 h. Cells were then treated with 20 ug/ml of CpG ODN2006 to activate TLR9. After 16 h, luciferase activity was measured and analyzed. These results are shown in FIG. 2.

The activity of SEQ ID NO:1 as an antagonist of TLR-9 requires higher concentrations than the inhibition of ICAM-1 expression. The comparative dose responses are shown in FIG. 3, in relation to the dose used in the enema formulation.

Figure 3:
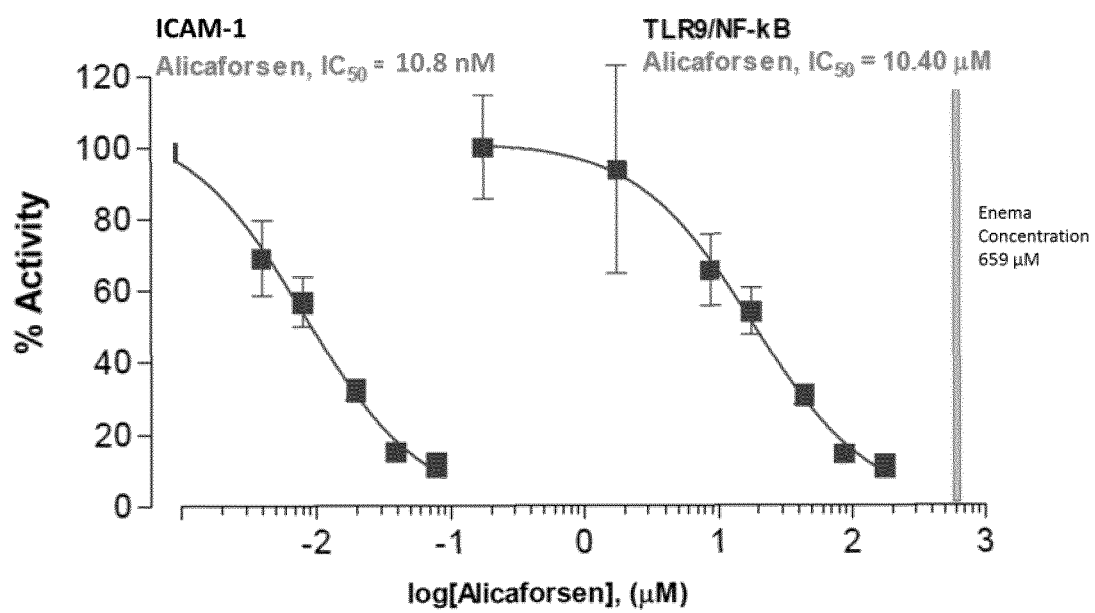
FIG. 3 is a graph showing SEQ ID NO:1 inhibition curves for ICAM-1 and TLR-9.

It is evident from the data of FIG. 3 that the therapeutic dose of SEQ ID NO:1 used for the treatment of IBD (659 uM) is sufficient to provide therapeutic levels of the drug for both mechanisms of action.

It was also necessary to rule out a direct inhibitory effect of SEQ ID NO:1 on the binding of the activator ODN2006. A screen of the two structures using the Oligo Analyzer 3.1 program (Integrated DNA Technologies, Inc.) showed that alicaforsen was energetically more likely to form a dimer with itself than with ODN2006. This comparison is shown in FIG. 4.

Figure 5:
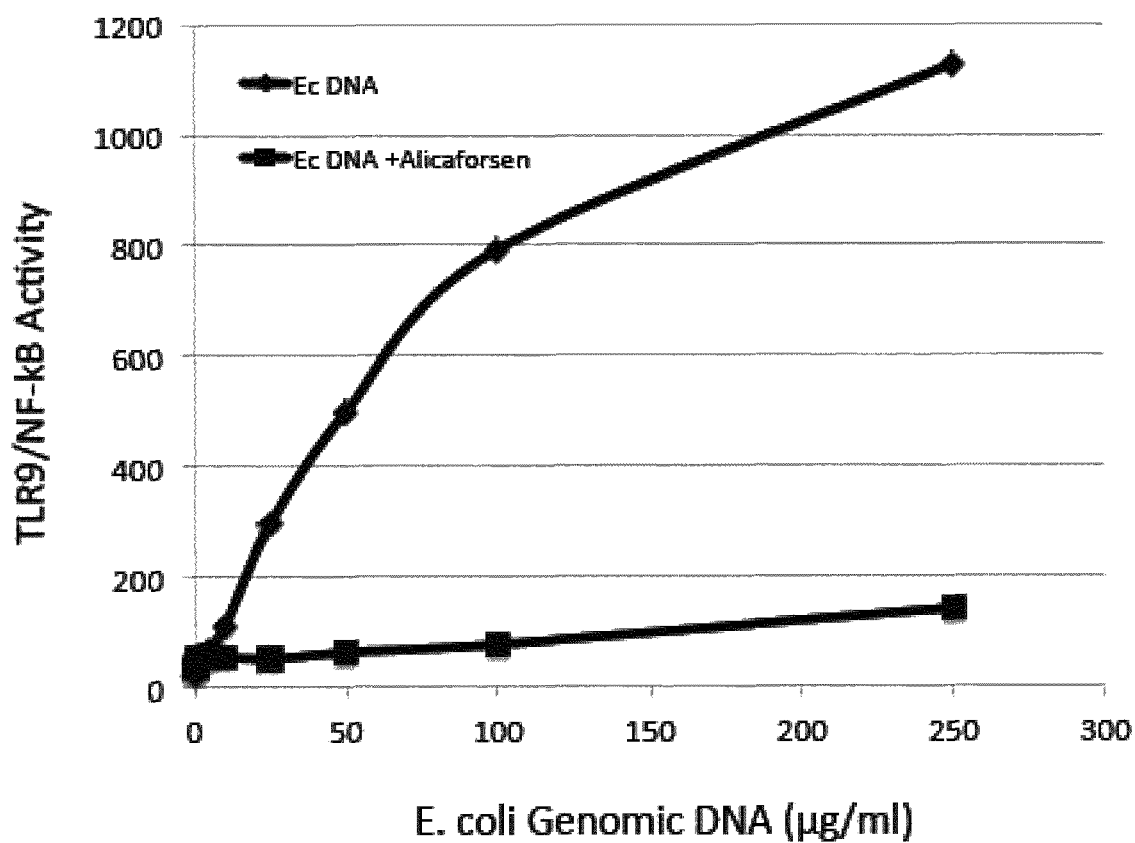
FIG. 5 is a graph showing the inhibition of TLR-9 activated by E coli genomic DNA.

While the data of FIG. 4 indicate that SEQ ID NO:1 is more likely to form a homodimer than a heterodimer with ODN2006, additional experiments tested the antagonist activity of SEQ ID NO:1 in the presence of *E. coli* genomic DNA as the activator. In this assay, SEQ ID NO:1 remained antagonistic to the activation of TLR-9 (FIG. 5).

Example 2: Prediction of Optimum Secondary Structure

The homodimer shown in FIG. 4 is the most energetically favorable duplex structure for SEQ ID NO:1. Of interest was whether this secondary structure may influence the TLR-9 inhibitory activity and under which conditions the duplex was most stable The predicted duplex structure is stabilized by 4 Watson-Crick type bonds flanked by G-A mismatches and another 2 G-C pairs. The CpG motifs remain unconstrained on the non-overlapping 3' ends for each duplex member.

SEQ ID NO:1 was therefore subjected to Circular Dichroism (CD) spectroscopy to gather information about the possible secondary structure. CD of DNA can be utilized to detect all 3 major forms of duplex structure (B, A and Z) and is sensitive to conditions that disrupt the structure such a heating. Of interest was the stability of any secondary structure detected at or above physiologic temperatures. Shown in FIG. 6 is the CD spectra of sample SEQ ID NO:1 in ddH20 at 4 C. The profile shows features characteristic of duplexes in the B-form of DNA, namely a characteristic low intensity positive band at ~280 nm, two low intensity negative bands at ~210 nm and ~255 nm and an positive intense band at ~190 nm The positive band at 190 nm was found to be sensitive to temperature between 4° C. and 20° C. Further heating to 80° C. showed a loss of >85% of the signal strength. This background signal was achieved at 40° C. making it unlikely that the structure is stable to physiological temperature under these conditions.

Additional thermal denaturation of the putative duplex was also studied in the presence of Na$^+$ at concentrations of 50 mM and 150 mM. Sodium fluoride was used as Cl$^-$ ions interfere with the CD spectra in this UV region.

Figure 7:
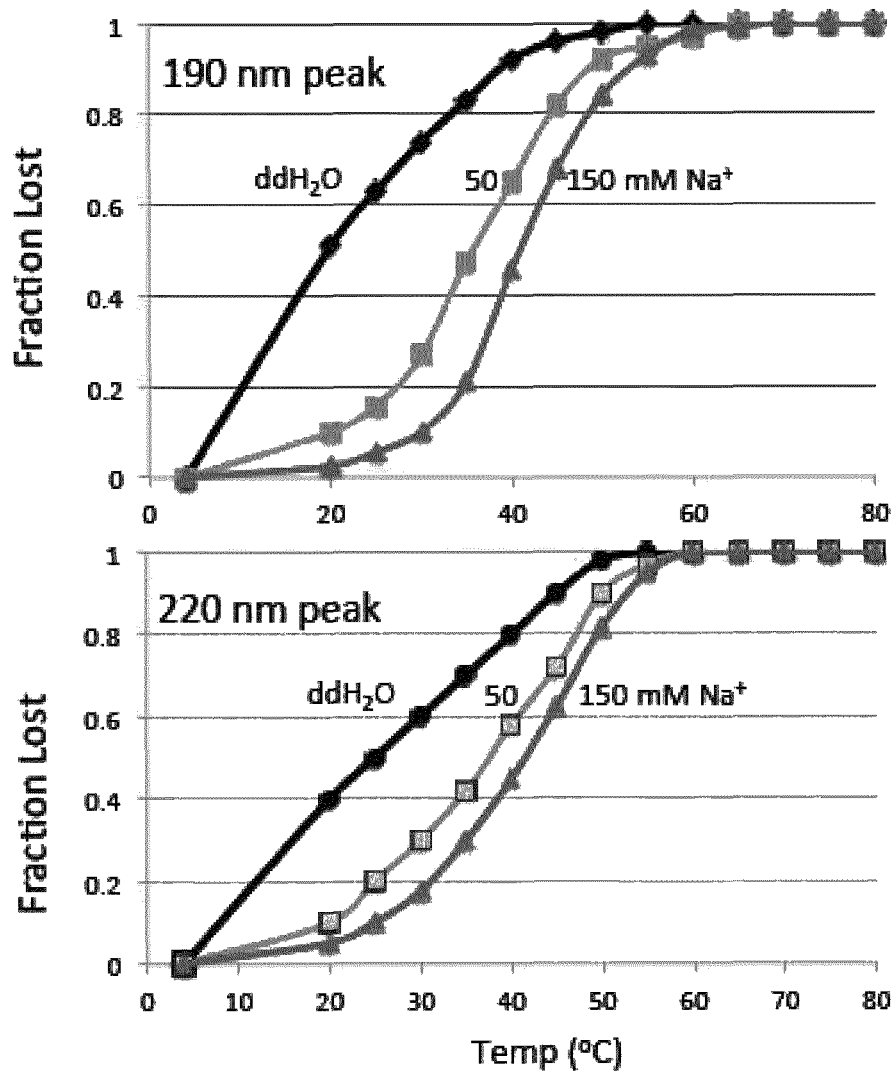
FIG. 7a shows a 190 nm peak intensity as a function of temperature.
FIG. 7b shows a 220 nm peak intensity as a function of temperature.

As can be seen in FIG. 7(*a*), the intensity of the 190 nm peak is more stable to heating under both 50 and 150 mM sodium conditions, retaining at least 50% of its structure to 40° C. In addition, the intensity of the 190 nm peak returned to pre-heated levels once the samples were cooled back to 20° C. This implies that the observed secondary structure is reversible after melting.

No significant changes in the negative peak at 210 nm were detected upon heating. However, the positive peak at 220 nm was found to respond similarly to that of the 190 nm peak. These data are shown in FIG. 7(*b*).

Figure 8:
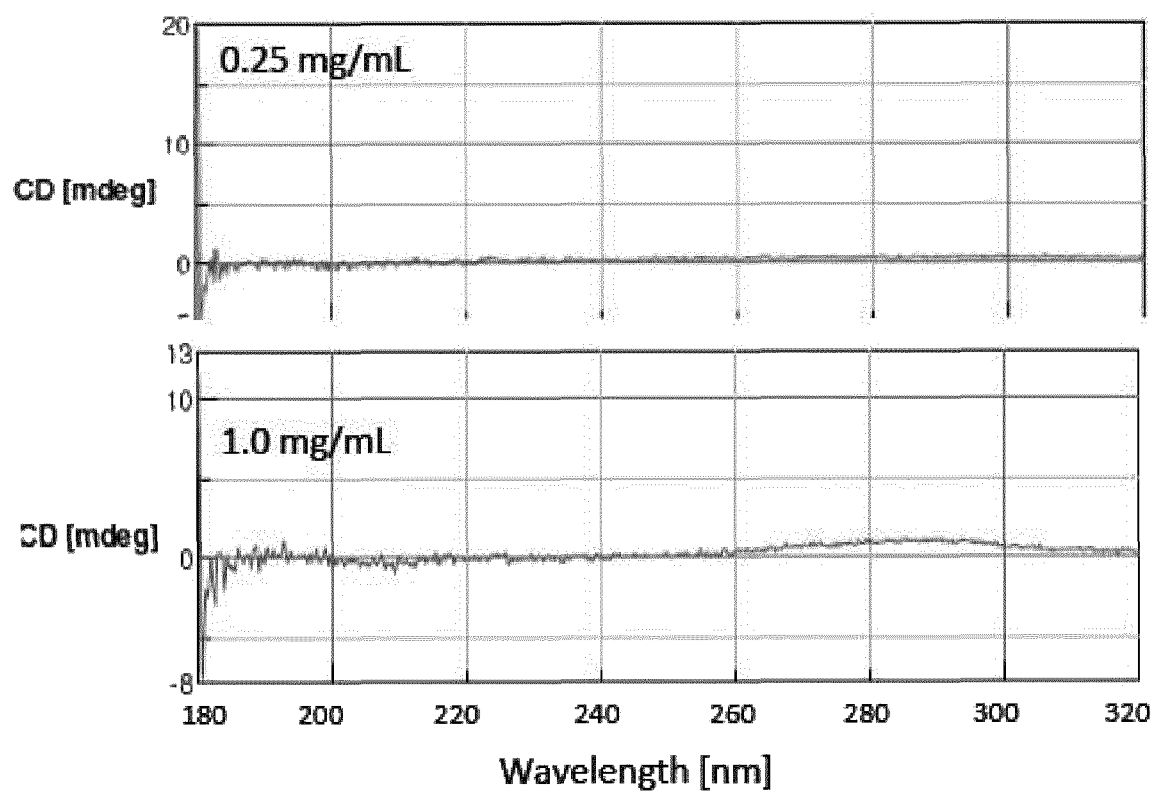
FIG. 8 shows the spectra of SEQ ID NO:1 in 5 mM spermine.

Additional experiments were conducted to test the influence of Mg$^{++}$ and polyamines on the stability of the structure. Surprisingly, the polyamine, spermine at 5 mM in the presence of 50 mM Na$^+$ completely abolished the secondary structure (FIG. 8).

This could be a function of the altered phosphate backbone of SEQ ID NO:1 which contains 20 sulfur substitutions in place of O— on each phosphate group (phosphorothioate).

Example 3: Influence of Structure Changes on TLR-9 Antagonism

Figure 9:
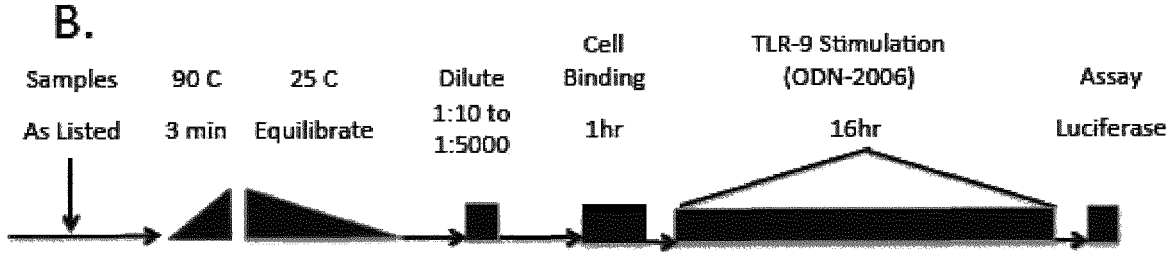
FIG. 9 shows a schematic of the experimental set up.

To test the effect of treatments known to stabilize and/or destabilize the secondary structure of SEQ ID NO:1 a series of experiments explored the effect of heat, Na+, Mg+ and spermine on the TLR-9 antagonist activity of SEQ ID NO:1. The samples and conditions of these tests are diagramed in FIG. 9.

Briefly, samples of SEQ ID NO:1 were dissolved in Tris buffer at pH 7.2 including 50 mM NaCl, in the presence of either 15 mM Mg$^{++}$ or 5 mM spermine or both Mg$^{++}$ and spermine. One sample remained at room temperature while the remaining samples were heated to 90° C. for 3 min and then allowed to cool to room temperature. The samples were then diluted to the indicated concentrations and incubated with the target cells for 1 hr, prior to the addition of 1.0 uM ODN2006 to stimulate TLR-9. The results of the experiment are shown in FIG. 10.

Figure 10:
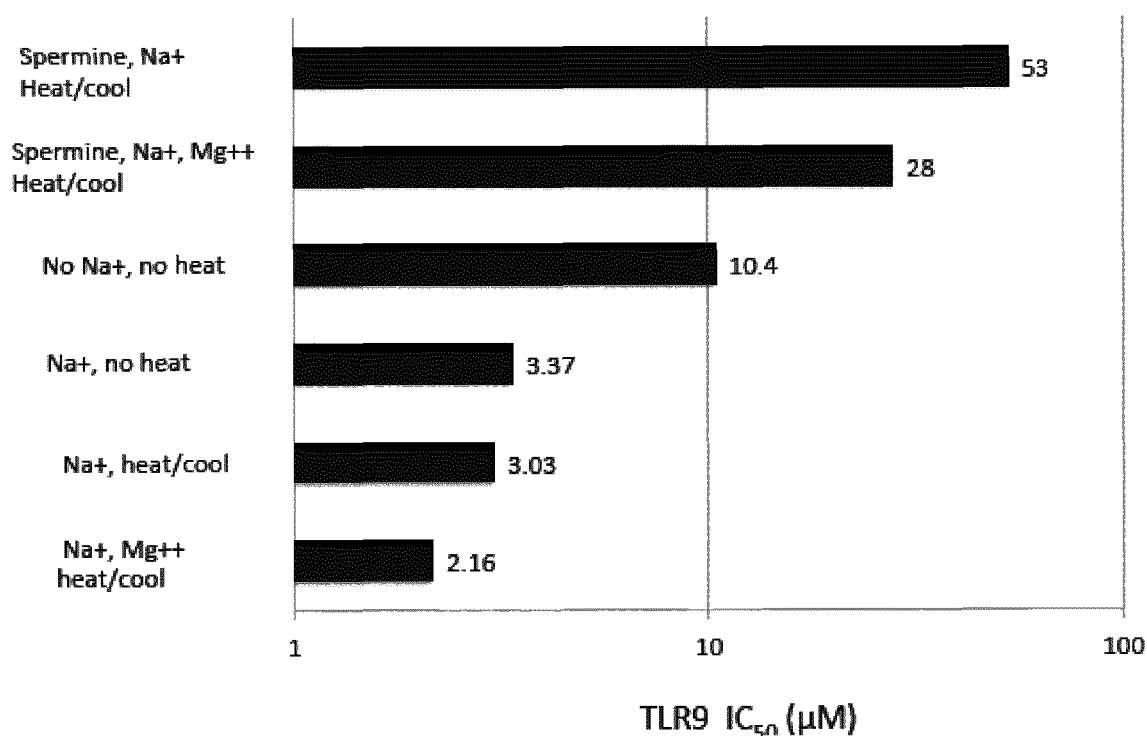
FIG. 10 shows IC50's for SEQ ID NO:1 inhibition of ODN2006 activation of TLR-9.

It can be seen in FIG. 10 that conditions which were observed to alter the secondary structure of SEQ ID NO:1 also influence its activity as an inhibitor of TLR-9. It is also noted that these conditions were maintained during the heating and cooling step where they had an opportunity to influence the secondary structure of SEQ ID NO:1. However, once diluted into the cell culture media, the conditions would be altered to those of the media and the temperature would revert to 37° C. The differences seen are therefore stable under normal physiological conditions.

This alteration of conditions, when the samples are incubated with cells, may be the reason that some activity is still observed in the spermine-treated samples, even though the CD spectra would indicate that the pre-incubation conditions removed the secondary structure of the duplex. Alternatively, the results seen with spermine could represent remaining TLR-9 inhibitory activity of non-duplexed molecules (monomers).

Example 4: Treatment of Inflammation of the Eye with Alicaforsen

To test the effect of SEQ ID NO:1 on the condition inflammation of the eye, the effect of two different concentrations of alicaforsen in a murine model of dry eye by scopolamine administration was investigated.

Dry Eye Murine Mouse Model

In a model of mice, the application of transdermal scopolamine patches to the mid-tail is used to reduce aqueous tear production and thus mimic lacrimal gland insufficiency. The function of scopolamine is to induce a pharmacologic blockade of cholinergic receptors in the lacrimal gland and therefore to decrease aqueous production. The desiccation is amplified by adding environmental stress Animals are exposed to a low-humidity environment and constant airflow.

Experimental Method

Animals Used in the Study:
 Species: Mouse.
 Strain: C57BL/6N (pigmented).
 Age: Approximately 6-7 weeks (at the first day of induction).
 Number/sex: 55 females (study 40; reserve 15).

Throughout the study, animals had free access to food and water. They were fed with a standard dry pellet diet. Tap water was available ad libitum from plastic bottles.

40 animals were included in this study. Animals were selected based on good health and homogeneous body weight. Only healthy animals without visible ocular defect (corneal opacity) were involved in this study. Animals were randomized into the study groups using a macro function in Excel® software on the basis of the mean of the corneal fluorescein staining scores from both eyes on Day 3.

Dry eye symptoms were induced in pigmented C57BL/6N mice by exposing them to a controlled environment room (approximate relative humidity <25%, temperature 22° C.±2° C.), in a cage with an air-flow around 15 L/min and transdermal scopolamine administration (0.5 mg/72 h) for eleven days.

Scopolamine Administration

Mice were treated with transdermal scopolamine administration (0.5 mg/72 h; Scopoderm TTS®). The transdermal scopolamine patch was wrapped near the tail base of the mouse, secured with cellophane tape. Patches were reapplied every 48 hours.

Route and Method of Administration and Justification

Mice were randomized into 4 groups of 10 animals. The study was divided into 2 experimental sets with 5 animals of each group represented. All mice were treated on day one and then treated for 10 days in total according to the following regime:

Optimmune® group: two doses per day on Days 3 and 10 and three doses per day on Day 4 to Day 9.
alicaforsen (10 mM and 1 mM) group: one dose per day.
Vehicle Group: one dose per day.

All test items, control items and comparator item were instilled in both eyes (5 μL per administration), using a micropipette.

Tear production and corneal defects were assessed at baseline, on Days 3, 6 and 10 using phenol red thread (PRT) and corneal fluorescence staining (CFS), respectively, for each animal of the 4 groups.

General Clinical Signs
  Body weights
  The body weight of all animals was recorded.
  General appearance
  Each day, the general clinical signs and the appearance of all animals was observed.
  Ocular examinations
  Two types of ocular examinations were conducted:
  A) Measurement of Aqueous Tear Production PRT Test.
  Tear production was measured with the PRT test (Zone-Quick, FCI-Ophthalmics) on both eyes, before administration on Day 3 and at least one hour after the second treatment for the other days of the study. The thread was placed in the lateral cantus of the lateral conjunctival fornix for 30 seconds. The thread wet by tears would turn red, indicated aqueous tear production. This data was expressed in millimetres.
  B) Corneal Fluorescein Staining (CFS)
  At the different time points the measurement was performed before administration on Day 3 and at least one hour after the second treatment for the other days of the study. The eyes of the animals from all groups were examined by slit-lamp observation using blue light after 0.5% fluorescein eye drop instillation (0.5 μL). Punctuate staining was recorded with the standardized National Eye Institute (NEI) grading system giving a 0-3 score to each of the 5 areas in which the corneas were divided.

Results:
Animal Behaviour and Body Weights
  A slight loss in body weight was observed for the majority of animals of all groups between Day 0 and Day 10 due to dry eye conditions.

alicaforsen (10 mM and 1 mM), Vehicle, and Optimmune® did not affect the behaviour of the animals.

PRT Test:
  On Day 3, the tear production decreased for all groups. The values of untreated group were stable until Day 10. These data showed a good induction of dry eye in this murine model.

Figure 11:
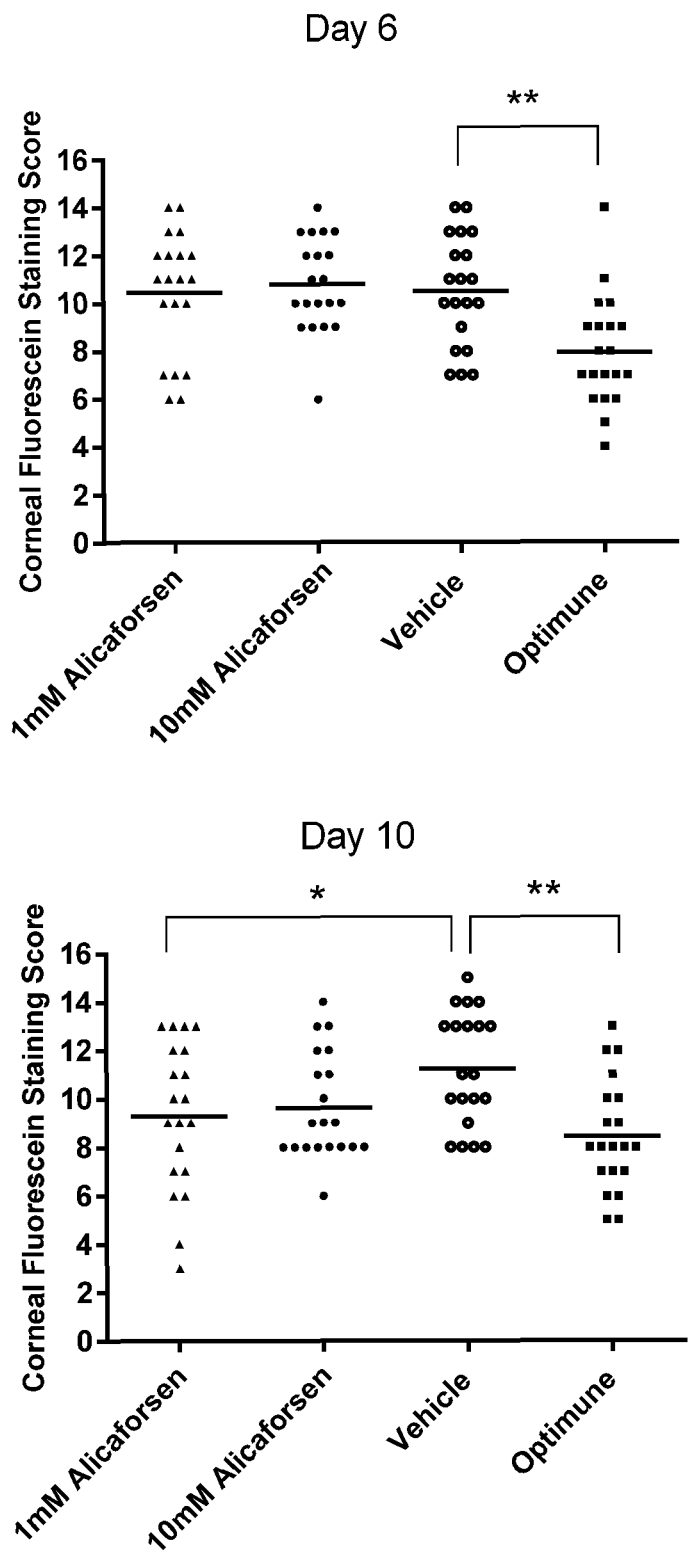
FIG. 11 shows the Conical Fluorescein Staining (CFS) evaluation of alicaforsen (1 mM and 10 mM dose) in scopolamine dry eye mouse model at day 6 and day 10. Each circle represents one eye and the line is the mean of the group. Two-way and one-way ANOVA Analyses were performed followed by Dunnett's Tests for multiple comparisons * $p<0.05$; ** $p<0.001$.

CFS Test:
  Results from the CFS are summarized in Table 1 below and in FIG. 11:

TABLE 1

| Dry eye symptoms evaluation | | |
|---|---|---|
| | Corneal fluorescein staining score (mean ± SD) | |
| Treatment | Day 6 | Day 10 |
| ALICAFORSEN (10 mM) | 10.8 ± 2.0 | 9.7 ± 2.2 |
| ALICAFORSEN (1 mM) | 10.5 ± 2.6 | 9.3 ± 3.1 |
| | | (p = 0.0429) |
| Vehicle (PBS) | 10.5 ± 2.3 | 11.3 ± 2.4 |
| Optimmune ® | 8.0 ± 2.3 | 8.5 ± 2.3 |
| | (p = 0.0021) | (p = 0.0020) |

Note:
Statistical analysis relative to Vehicle group with Dunn's multiple comparison tests: $p < 0.05$.

The Vehicle group had dry eye symptoms from Day 3 to Day 10, showing that this study is validated.

CFS Scores:
  The group treated with Optimmune® showed corneal fluorescein staining scores lower than the Vehicle group on Day 6 (p=0.0021) and Day 10 (p=0.0020).
  The groups treated with alicaforsen (1 mM and 10 mM) had similar corneal fluorescein staining scores to Vehicle group on Day 6.
  The groups treated with alicaforsen (1 mM and 10 mM) showed corneal fluorescein staining scores lower than the Vehicle group on Day 10 and the group treated with alicaforsen (1 mM) showed a significant difference (p=0.0429) compared to vehicle. Under these experimental conditions, multiple topical administrations of alicaforsen (1 mM and 10 mM) were clinically well tolerated.

The Vehicle group had dry eye symptoms from Day 3 to Day 10, showing that this study is validated.

Optimmune® 0.2% and alicaforsen (1 mM) groups showed a statistically significant reduction in the dry eye symptoms as measured by corneal fluorescein staining Example 5: Treatment of Asthma with Alicaforsen To test the effect of alicaforsen on conditions such as asthma, an ovalbumin (OVA)-induced allergic asthma mouse model was treated with alicaforsen.

Method:
  Allergic asthma was modeled in female BALB/c mice by initial sensitization to OVA followed by subsequent intranasal challenge of purified OVA.
  Mice were monitored throughout the study for changes in body weight and general signs of sickness. Allergic response to OVA was measured by examining bronchoalveolar lavage fluid (BALF) for inflammatory cell influx and the presence of the inflammatory cytokine IL-13.
  Additionally, animals in experimental groups were treated via intranasal (IN) administration of either alicaforsen, at 1 mM dosing concentration, control vehicle (PBS), or intraperitoneal (IP) dexamethasone as a positive anti-inflammatory control. Test Materials Test Item(s)
  Table 2 and 3 below detail the test items and test materials used during the study.

TABLE 2

| Material | Name | Cat. No. | Lot No. | Manufacturer | Storage Condition | Exp. Date |
|---|---|---|---|---|---|---|
| Positive Control | Dexamethasone | NDC 63323-165-05 | P355990 | APP Pharmaceuticals | 18-22° C. | April 2018 |
| Sensitization/Challenge | OVA, endotoxin-free | LS003059 | 55P16242 | Worthington | 2-8° C. | December 2017 |

TABLE 3

| Material | Name | Cat. No. | Lot No. | Manufacturer | Storage Condition | Exp. Date |
|---|---|---|---|---|---|---|
| Positive Control | Dexamethasone | NDC 63323-165-05 | P355990 | APP Pharmaceuticals | 18-22° C. | April 2018 |
| Sensitization/Challenge | OVA, endotoxin-free | LS003059 | 55P16242 | Worthington | 2-8° C. | December 2017 |
|  | Aluminum Hydroxide gel | Vac-alu-250 | 5295 | Invivogen | 18-22° C. | May 2018 |
|  | PBS | 10010031 | RN13F2486 | Life Technologies | RT | February 2018 |
| Anesthesia Item | Isofluorane | NDC 66794-013-25 | B57D16A | Piramal Healthcare | 18-22° C. | March 2021 |
| Multiplex kit | Mouse Cytokine/Chemokine magnetic Bead panel | MCYTOMAG-70K | 2990274 | Millipore | 2-8° C. | July 2018 |

Dosing of alicaforsen at a concentration of 1 mM was prepared based on a 0.878 drug content factor and MW of 6795.9 g/mol. Prepared solutions were stored at 2-8° C. for the duration of the study.

1 mL dexamethasone stock solution (4 mg/mL) was added to 3 mL saline for a solution concentration of 1 mg/mL.

OVA/Alum for Sensitisation:

Chicken egg OVAlbumin (OVA) was dissolved in PBS to a concentration of 1 mg/mL. 1 mg/mL OVA solution was diluted 1:1 in Alum adjuvant and stored at 2-8° C. overnight until use. Final dosing concentration was 100 µg OVA per 200 µL OVA/alum mixture.

OVA for Challenge:

1 mL sterile PBS was added to 10 mg OVA for a solution concentration of 10 mg/mL.

0.35 mL OVA stock solution was added to 1.75 ml PBS for a solution concentration of 1.67 mg/mL. Final dosing concentration=50 µg OVA in 30 µL.

Animals Used in the Study:

| | |
|---|---|
| Species/Strain: | Balb/c |
| Gender: | Female |
| Total # of Animals: | 55 |
| Age: | 7-8 weeks of age at study initiation. |
| Body Weight: | Weight variation of the animals at study initiation did not exceed ±20% of the mean weight. |
| Animals Health: | The health status of the animals used in this study was examined on arrival. All animals were in good health, were acclimatized to laboratory conditions, and were used in the study. |
| Acclimation: | At least 72 hours. |
| Housing: | During acclimation and study, animals were housed within a limited access rodent facility and kept in groups of maximum 5 mice. Mice were housed in sterilized individually ventilated polysulfone cages with irradiated cob bedding material. |
| Food and Water: | Animals were provided ad libitum a commercial rodent diet and free access to drinking water, supplied to each cage via sterilised polyethylene bottles. All food and water is sterilised. |
| Environment: | Automatically controlled environmental conditions were set to maintain temperature at 20-26° C. with relative humidity (RH) of 30-70%, a 12:12 hour light:dark cycle. |
| Randomisation: | Animals were randomly assigned to cages on arrival. Animals were assigned to treatment groups on day −1. |
| Termination: | Euthanasia anesthesia overdose. |

Test Groups

The table 4 below lists the experimental group(s) used in the study.

TABLE 4

| Group Number | Group Size | Group Description | Disease Induction | T1/vehicle Route | T1/vehicle Dose Level | T1/vehicle Volume Dosage | T1/vehicle Dosing Regime |
|---|---|---|---|---|---|---|---|
| 1 | N = 5 | Naive | N/A | N/A | N/A | N/A | N/A |
| 2 | N = 10 | Disease Only | Sensitization with | NA | NA | NA | NA |
| 3 | N = 10 | Vehicle | OVA/Alum via ip | IN | NA | 30 µl | Once daily on |
| 4 | N = 10 | Dexamethasone | injection on day 0 | IP | 10 mg/kg | 10 ml/kg | study days 14, |

TABLE 4-continued

| Group Number | Group Size | Group Description | Disease Induction | T1/vehicle Route | T1/vehicle Dose Level | T1/vehicle Volume Dosage | T1/vehicle Dosing Regime |
|---|---|---|---|---|---|---|---|
| 5 | N = 10 | Alicaforsen | and 14, and challenged with OVA in PBS intranasal on days 14, 25-27. | IN | 1 mM | 30 µl | 25-27. |

Figure 12:
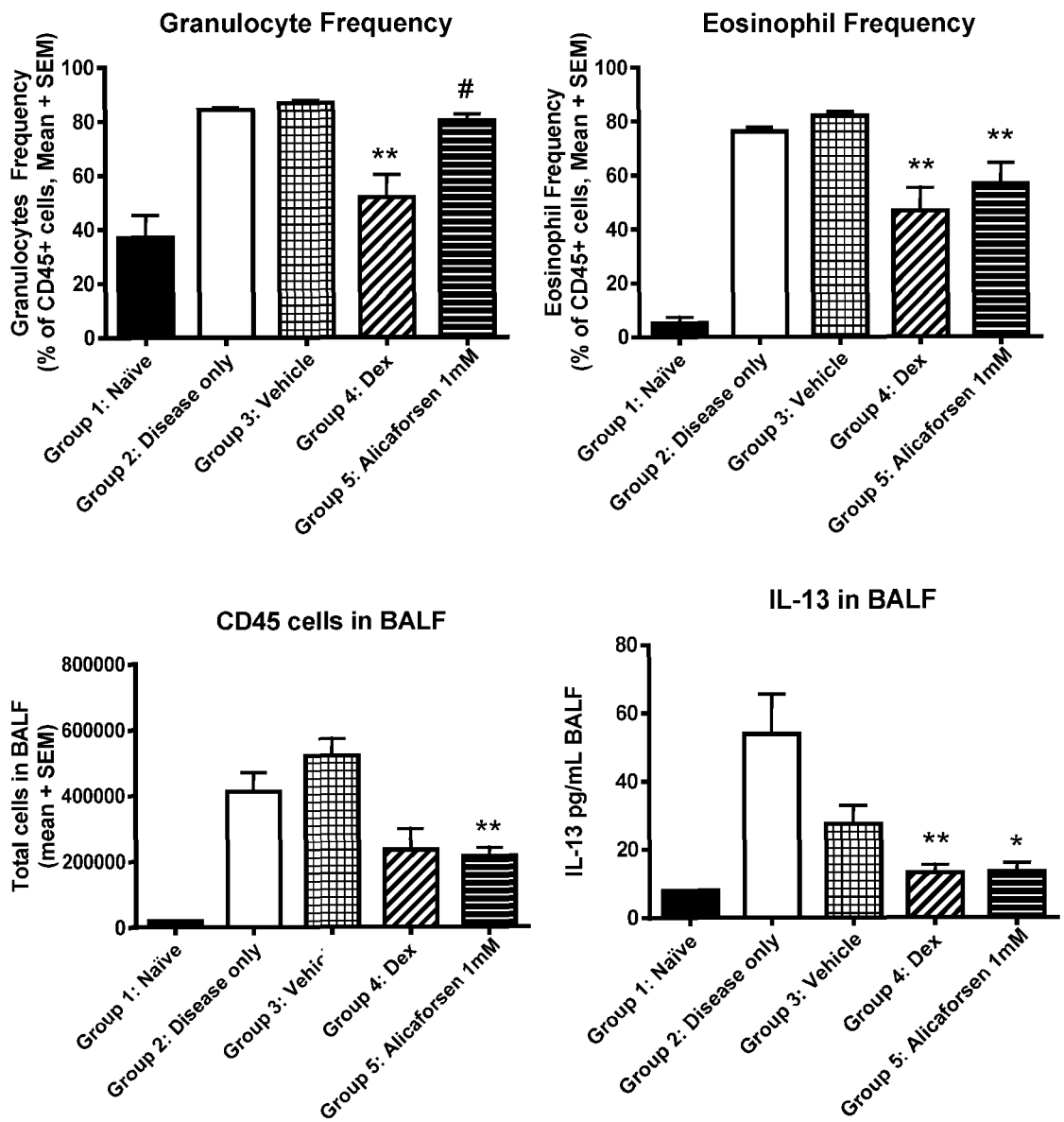
FIG. 12 shows the evaluation of alicaforsen in Ovalbumin-Induced Murine Model of Allergic Asthma. One-way ANOVA followed by Dunnett's multiple comparison test compared to vehicle control; *$p<0.05$; ** $p<0.01$. Student's unpaired, two-tailed T-test comparing 1 mM alicaforsen to vehicle control; #$p<0.05$.

Disease Induction (Groups 2-6):
Ova Sensitisation:
On days 0 and 14, each animal was administered an IP injection of 200 µL OVA/Alum emulsion containing 100 µg OVA.
Ova Challenge:
On days 14 and 25-27, each animal was administered an intranasal challenge of 30 µL PBS containing 50 µg OVA.
Treatment with Test Item:
alicaforsen was administered at 1 mM concentration intra-nasally (IN) in a volume of 30 µL. Treatments were performed on the same days as OVA challenge on Study Days 14 and 25-27 (4 total treatments). Treatments were administered 1 hour following OVA challenge.
Positive Control Treatment:
10 mg/kg dexamethasone was administered in 200 µL volume/animal (intraperitoneal) on Study Days 14 and 25-27 (4 total treatments).
Observations and Examinations:
Clinical Signs:
Careful examinations were carried out daily. Observations for changes in skin, fur, eyes, mucus membranes, occurrence of secretions and excretions and autonomic activity were included. Significant changes in gait, posture, and response to handling, or the presence of bizarre behavior, tremors, convulsions, sleep and coma were recorded.
Body Weight:
Body weight of animals was determined shortly before the study commencement and twice weekly thereafter.
Termination, Tissue Sampling and Subsequent Analyses:
On Day 28, all mice were euthanised via detamine+ xylazine overdose and exsanguination.
BALF Collection and Analysis:
Bonchoalveolar lavage was performed on euthanised animals Briefly, an angiocatheter was placed into trachea. 1 mL of PBS was instilled into the lungs and allowed to flow back out into the syringe; the PBS was then instilled and removed again. The resultant Bronchoalveolar lavage fluid (BALF) was centrifuged at 500×g for 5 mins.
The non-cellular portion of the BALF was stored at −80° C. The levels of IL-13 were analyzed by Luminex technology.
The cellular portion of the BALF was used to analyze the cell influx. The total number of leukocytes within the BALF and different cell types present were examined via flow cytometry.
Granulocytes: $CD45^+$; Non-autofluorescent; $Gr-1^+$
Eosinophils: $CD45^+$; Non-autofluorescent; $Gr-1^+$; Siglec $F^+$ Results:
Animals sensitized and challenged with OVA protein showed signs of disease at experiment termination, including significantly increased alveolar influx of total leukocytes, granulocytes and eosinophils when compared to naïve mice. Furthermore, diseased animals showed significantly increased levels of IL-13 in BALF.
Treatment with the positive control dexamethasone significantly reduced granulocyte and eosinophil populations and IL-13 levels in the BALF, indicating a reduction in the allergic response to OVA.
Intranasal administration of alicaforsen (1 mM) resulted in significantly lower levels of total leukocytes (CD45+ cells) in the BALF and significantly reduced the proportion of eosinophils. There was also a significant reduction in total granulocyte frequency in 1 mM alicaforsen treated group compared to the vehicle group. Additionally, treatment with 1 mM alicaforsen led to significantly lower IL-13 levels in the BALF. These data indicated a reduction in allergic response to OVA.
The results are shown in FIG. 12 and in Table 5 below, the results demonstrate the anti-inflammatory effect of alicaforsen on a murine model of allergic asthma.

TABLE 5

Flow analysis of BALF mean, standard error of the mean (SEM) and IL-13 expression in BALF mean (SEM).

|  | Granulocyte (Frequency of CD45+) | | Eosinophil (Frequency of CD45+) | |
|---|---|---|---|---|
|  | Mean | SEM | Mean | SEM |
| Group 1: Naive | 37.14** | 8.17 | 5.16** | 2.36 |
| Group 2: Disease only | 84.23 | 0.92 | 76.23 | 1.63 |
| Group 3: Vehicle | 86.69 | 1.22 | 81.97 | 1.69 |
| Group 4: Dexamethasone | 51.88** | 8.53 | 46.60** | 8.70 |
| Group 5: alicaforsen 1 mM | 80.16# | 2.56 | 56.64**,## | 8.02 |

|  | Total CD45 cells in BALF | | BALF IL-13 pg/ml | |
|---|---|---|---|---|
|  | Mean | SEM | Mean | SEM |
| Group 1: Naive | 20186** | 1095 | 8.0** | 0.0 |
| Group 2: Disease only | 413776 | 57945 | 53.8 | 11.8 |
| Group 3: Vehicle | 521708 | 51727 | 27.5 | 5.5 |
| Group 4: Dexamethasone | 236574 | 63225 | 13.2** | 2.3 |
| Group 5: alicaforsen 1 mM | 217303**,## | 26340 | 13.4*,# | 2.6 |

The invention claimed is:

1. A pharmaceutical composition comprising:
an oligonucleotide of SEQ ID NO:1;
Na+; and
Mg++.

2. The composition as claimed in claim 1, further comprising one or more of hydroxymethyl cellulose, methyl paraben sodium, propylparaben sodium, monobasic sodium phosphate monohydrate, sodium hydroxide, hydrochloric acid and/or water.

3. The composition as claimed in claim 1, wherein the composition is in the form of a liquid syrup, gel, film, cream, powder, tablet and/or enema.

4. The composition as claimed in claim 1, wherein the composition comprises the following components in the following ranges:

| | |
|---|---|
| the oligonucleotide of SEQ ID NO: 1 | 4 mg/ml |
| hydroxymethyl cellulose | 7-8 mg/ml |
| methylparaben sodium 16.6 mM | 2.8-3.0 mg/ml |
| propylparaben sodium 1.4 mM | 0.28-3 mg/ml |
| monobasic sodium phosphate monohydrate 37.5 mM | 4.4-4.6 mg/ml. |

5. A medicament, comprising the composition as claimed in claim 1 and a pharmaceutically-acceptable carrier.

6. A method of making the composition as claimed in claim 1, the method comprising combining the oligonucleotide of SEQ ID NO:1 with the Na+ and the Mg++.

7. The composition, as claimed in claim 1, wherein the composition is in the form of an enema and wherein the composition is formulated in a dosage form to provide a concentration of the oligonucleotide of SEQ ID NO:1 at 2 mg/ml per day.

8. The composition, as claimed in claim 1, wherein the composition is in the form of an enema and wherein the composition is formulated in a dosage form to provide a concentration of the oligonucleotide of SEQ ID NO:1 at 1-4 mg/ml per day.

9. The composition as claimed in claim 1, wherein the Na+ is included at 40-200 mM.

10. The composition as claimed in claim 1, wherein the Na+ is included at 100-190 mM.

11. The composition as claimed in claim 1, wherein the Mg++ is included at 2-20 mM.

12. The composition as claimed in claim 1, wherein the Na+ is included at 140-160 mM.

13. The composition as claimed in claim 1, wherein the Na+ is included at 40-200 mM and the Mg++ is included at 2-20 mM.

14. The composition as claimed in claim 1, wherein the oligonucleotide contains at least one phosphorothioate backbone modification.

15. The composition as claimed in claim 1, wherein the Na+ is included at 40-200 mM, the is Mg++ is included at 2-20 mM, and the oligonucleotide contains at least one phosphorothioate backbone modification.

16. The composition as claimed in claim 1, wherein the oligonucleotide contains 20 phosphorothioate backbone modifications.

17. The composition as claimed in claim 1, wherein the Na+ is included at 23-11,495 μg per mg of the oligonucleotide of SEQ ID NO:1 and the Mg++ is included at 1.25-1215 μg per mg of the oligonucleotide of SEQ ID NO:1.

18. The composition as claimed in claim 1, wherein the Na+ is included at 230-1150 μg per mg of the oligonucleotide of SEQ ID NO:1 and the Mg++ is included at 12-122 μg per mg of the oligonucleotide of SEQ ID NO:1.

19. The composition as claimed in claim 1, wherein the composition comprises the following components in the following ranges:

| | |
|---|---|
| the oligonucleotide of SEQ ID NO:1 | 4 mg/ml |
| methylparaben sodium 16.6 mM | 2. 8-3.0 mg/ml |
| propylparaben sodium 1.4 mM | 0.28-3 mg/ml |
| monobasic sodium phosphate monohydrate 37.5 mM | 4.4-4.6 mg/ml. |

20. A medicament for use in the treatment of inflammatory disease in a mammalian subject by (i) suppressing innate immune response through inhibition of toll-like receptor 9 (TLR-9) and (ii) inhibiting influx of inflammatory cells through down-regulation of intracellular adhesion molecule 1 (ICAM-1), the medicament comprising:
    a pharmaceutically-acceptable carrier; and
    a pharmaceutical composition comprising:
        an oligonucleotide of SEQ ID NO:1 in an amount sufficient to (i) suppress innate immune response through inhibition of toll-like receptor 9 (TLR-9) and (ii) inhibit influx of inflammatory cells through down-regulation of intracellular adhesion molecule 1 (ICAM-1), in the mammalian subject to which the medicament is administered;
    Na+; and
    Mg++.

21. A method, comprising administering the composition as claimed in claim 1 to a subject.

22. A method, comprising administering the medicament as claimed in claim 5 to a subject.

23. A method, comprising administering the medicament as claimed in claim 20 to a subject.

\* \* \* \* \*

SEQUENCE LISTING

<160> NUMBER OF SEQ ID NOS: 5

<210> SEQ ID NO 1
<211> LENGTH: 20

```
<212> TYPE: DNA
<213> ORGANISM: Homo sapiens

<400> SEQUENCE: 1
gcccaagctg gcatccgtca                                              20

<210> SEQ ID NO 2
<211> LENGTH: 20
<212> TYPE: DNA
<213> ORGANISM: Homo sapiens

<400> SEQUENCE: 2
cctgacggat gccagcttgg                                              20

<210> SEQ ID NO 3
<211> LENGTH: 19
<212> TYPE: DNA
<213> ORGANISM: Homo sapiens

<400> SEQUENCE: 3
cccaagctgg catccgtca                                               19

<210> SEQ ID NO 4
<211> LENGTH: 19
<212> TYPE: DNA
<213> ORGANISM: Homo sapiens

<400> SEQUENCE: 4
gcccaagctg gcatccgtc                                               19

<210> SEQ ID NO 5
<211> LENGTH: 13
<212> TYPE: DNA
<213> ORGANISM: Homo sapiens

<400> SEQUENCE: 5
gcccaagctg gca                                                     13
```